(12) United States Patent
Wang

(10) Patent No.: US 10,859,530 B2
(45) Date of Patent: Dec. 8, 2020

(54) DETECTION DEVICE FOR ION COUNT IN TUMOR-RELATED MOLECULES AND USAGE METHOD THEREOF

(71) Applicant: Jian Wang, Jiangsu (CN)

(72) Inventor: Jian Wang, Jiangsu (CN)

( * ) Notice: Subject to any disclaimer, the term of this patent is extended or adjusted under 35 U.S.C. 154(b) by 7 days.

(21) Appl. No.: 16/458,137

(22) Filed: Jun. 30, 2019

(65) Prior Publication Data

US 2019/0331641 A1    Oct. 31, 2019

Related U.S. Application Data

(63) Continuation of application No. PCT/CN2017/109525, filed on Nov. 6, 2017.

(30) Foreign Application Priority Data

Nov. 2, 2017  (CN) .......................... 2017 1 1064618
Nov. 2, 2017  (CN) .......................... 2017 2 1445184

(51) Int. Cl.
*G01N 27/64*       (2006.01)
*G01N 33/483*      (2006.01)

(52) U.S. Cl.
CPC .......... *G01N 27/64* (2013.01); *G01N 33/4833* (2013.01)

(58) Field of Classification Search
CPC ............................ G01N 27/64; G01N 33/4833
See application file for complete search history.

(56) References Cited

U.S. PATENT DOCUMENTS

| 5,425,374 A | * | 6/1995 | Ueda .................... A61B 5/0836 422/84 |
| 6,794,645 B2 | | 9/2004 | Kanik |

FOREIGN PATENT DOCUMENTS

| CN | 102138070 A | 7/2011 |
| CN | 102565183 A | 7/2012 |
| CN | 202649167 U | 1/2013 |
| CN | 104377108 A | 2/2015 |
| CN | 106137204 A | 11/2016 |

* cited by examiner

*Primary Examiner* — Edwin C Gunberg
(74) *Attorney, Agent, or Firm* — Wayne & Ken, LLC; Tony Hom

(57) ABSTRACT

Disclosed is a detection device for an ion count in tumor-related molecules and a usage method thereof. The detection device comprises an air sample chamber (1), a first solenoid valve (2), an ionization chamber (3), a filament (4), a second solenoid valve (5), a vacuum generator (6), a high-voltage accelerating electrode (7), an ion collecting electrode (8) and an ion counter (9). The air sample chamber (1) is connected to the ionization chamber (3) through the first solenoid valve (2). The filament (4) is arranged at a left end of the ionization chamber (3). A lower end of the ionization chamber (3) is connected to the vacuum generator (6) through the second solenoid valve (5). The high-voltage accelerating electrode (7) and the ion collecting electrode (8) are successively arranged at a right end of the ionization chamber (3). The ion collecting electrode (8) is connected to the ion counter (9).

6 Claims, 5 Drawing Sheets

US 10,859,530 B2

DETECTION DEVICE FOR ION COUNT IN TUMOR-RELATED MOLECULES AND USAGE METHOD THEREOF

CROSS-REFERENCE TO RELATED APPLICATIONS

This application is a continuation of International Application No. PCT/CN2017/109525, filed on Nov. 6, 2017, which claims priority from Chinese Patent Application No. 201711064618.4, filed on Nov. 2, 2017 and No. 201721445184.8, filed on Nov. 2, 2017, all of which are hereby incorporated by reference in their entireties.

TECHNICAL FIELD

The present invention relates to the field of ion detection and in particular to a detection device for an ion count in tumor-related molecules and a usage method thereof.

BACKGROUND OF THE PRESENT INVENTION

In the prior art, B-ultrasonography, CT, biopsy, etc., are known as methods for detecting cancers. These detection methods may cause some injuries to the human bodies although they can detect the presence of diseases. By B-ultrasonogram, lesions can be shown and observed continuously from various angles and orientations. This helps in obtaining the position of a tumor and its relationship with the surrounding tissues and organs. However, B-ultrasonography has a narrow application range. CT is widely applied in tumor detection in parts such as brain, liver and pancreas. By CT, the areas involved by a lesion can be determined. However, the apparatuses for CT are expensive, and overexposure to CT-related radiation has a risk of inducing malignant tumors, leukemia and the like. With regard to biopsy, there is a possibility of needle-path implantation and cancer bleeding. Furthermore, these detection methods are less sensitive to early-stage cancers. Therefore, it is in urgent need for a cancer screening method that is simple and efficient, with little trauma.

Animal experiments show that, some cancers will give off a volatile odor which, animals may respond to, although are unrecognizable by human beings. The odor is defined as follows: odor=air+smell. "Air" means gas, which is a volatile matter. It is a substance, usually having small molecules, so it is very likely to become gas. "Smell" means senses. It works as a sensor. It refers to the change in physical quantities (they may be electricity, magnetism, light, length or volume, a stream of ions, a stream of molecules, etc.) after molecules act on the surface of the senses (sensors). Therefore, odor is not a substance. Exactly, it is a process that substances interact with each other. It was reported in the Lancet (a leading medical journal) in 1989 and 2001 that dogs can recognize melanoma. It was also reported in BMJ (British Medical Journal) in 2004 that dogs can distinguish urine from a patient with bladder cancer from urine from a patient without bladder cancer. In 2006, it was found by scholars that common domestic dogs, after being trained, can distinguish a lung cancer or breast cancer sample from a normal sample by odor. In 2008, it was further found by scholars that dogs can distinguish ovarian cancer tissues from control tissues. Therefore, it is indicated that some cancers can give off a volatile odor representative of tumor-related molecules.

SUMMARY OF THE PRESENT INVENTION

The presence of tumor-related molecules in the exhaled air has been proved by many experiments in other countries. The tumor molecules consist of related tumor atoms. Atoms can be ionized into ions and electrons. The ions can be counted to obtain a count value related thereto. This count value (i.e., the peak shown in the chart of an ion count in the tumor-related molecules) reflects the presence and number of certain tumor-related molecules in the exhaled air. The detection of tumor-related molecules is realized.

To overcome the deficiencies of the prior art, an objective of the present invention is to provide a detection device for an ion count in tumor-related molecules and a usage method thereof. By the detection device, from the air exhaled by a patient, a determination about whether the patient has cancer and the development of the cancer can be made quickly. The detection is fast and will cause no injury to the subject.

For this purpose, the present application employs the following technical solutions.

A detection device for an ion count in tumor-related molecules is provided, comprising an air sample chamber, a first solenoid valve, an ionization chamber, a filament, a second solenoid valve, a vacuum generator, a high-voltage accelerating electrode, an ion collecting electrode and an ion counter. The gas sample chamber is connected to the ionization chamber through the first solenoid valve. The filament is arranged at a left end of the ionization chamber. A lower end of the ionization chamber is connected to the vacuum generator through the second solenoid valve. The high-pressure accelerating electrode and the ion collecting electrode are successively arranged at a right end of the ionization chamber. The ion collecting electrode is connected to the ion counter.

The air sample chamber is configured to collect the air exhaled by a subject. The first solenoid valve is communicated with the air sample chamber and the ionization chamber, and configured to control the flow of the air from the air sample chamber to the ionization chamber. The filament is connected to a negative pole of a high-voltage electric field, to serve as a cathode. The high-voltage accelerating electrode is of a net structure. This is advantageous for the passing of electrons. The ion collecting electrode is a graphene electrode. Graphene is quite stable in structure, since it is an elemental carbon formed by the neat arrangement of carbon atoms in a hexagonal lattice. Graphene has only one layer of atoms. The motion of electrons is limited in one plane. It is quite suitable to be used as an ion collecting electrode.

In the circuit in the ionization chamber, a fundamental frequency power supply is rectified and filtered to obtain a DC voltage; the DC voltage is converted into a high-frequency voltage by a main inverter circuit; the high-frequency voltage is passed to a primary side of a high-voltage transformer in a high-voltage generator and boosted by the high-voltage transformer; and the AC high-frequency voltage obtained at the primary side is converted into a constant DC high-voltage by voltage-doubling rectification. The constant DC high-voltage is the accelerating electrode high voltage. An accelerating electrode sampling signal is compared with a set value in real time. An error signal controls, after pulse width modulation, the ON time of an inverter bridge, in order to ensure the actual value of the accelerating electrode is equal to the set value. A fundamental frequency power supply is rectified and filtered to obtain a DC voltage, the DC voltage is passed to a filament inverter circuit and then to the primary side of a filament transformer, and the output from the primary side is used as the filament heating voltage. The filament heating current is regulated by PWM. During the measurement, the current sampling signal of the filament is compared with a set value in real time. An error signal controls, after pulse width modulation, the width of the inversion trigger pulse of the filament, in order to ensure the actual value is equal to the set value. The voltage value of the accelerating electrode high voltage is regulated, tumor molecules are ionized by different voltages, and the result of ionization is analyzed by the ion counter. In this way, the sorted detection of tumor-related molecules is completed. Corresponding to the accelerating electrode high voltage having different voltage values, the filament current may be regulated accordingly, in order to improve the efficiency of ion counting.

The filament heating circuit functions to emit electrons. The measurement current for the ionization chamber is related to two factors: the filament current and the accelerating electrode voltage. When the accelerating electrode voltage changes, the strength of the in-line accelerated electric field changes, the capability of the accelerating electrode in collecting electrons changes correspondingly, so that the accelerating electrode current changes. The change in the voltage of the filament causes the change in the current of the filament, directly influencing the efficiency of emitting electrons by the filament. The degree of vacuum inside the ionization chamber is maintained above 10-6 mmHg, in order to ensure the normal heating of the filament and the speed of the electrons flying to the anode.

The measurement current in the ionization chamber is determined by the current of the high-voltage accelerating electrode. The current of the high-voltage accelerating electrode depends upon the number of electrons emitted by the filament in a unit time. The number of electrons emitted by the filament is determined by the temperature of the filament. At a higher temperature of the filament, more electrons will be emitted by the filament. The temperature of the filament is determined by the filament heating voltage in the ionization chamber. Under a higher filament heating voltage, the temperature of the filament will be higher. In order to ensure the precision of ion counting, the current for the filament and the high-voltage accelerating electrode in the ionization chamber is always maintained unchanged.

The measurement circuit is an inverting amplifier consisting of operational amplifiers. Its in-phase input terminal is grounded. According to the principle of dummy ground, the potential of its inverting input terminal is also 0, thereby ensuring that the potential of the ion collecting electrode is 0. As an important characteristic of a deep parallel voltage negative feedback amplifier, "dummy ground" means that the input terminal of an integrated operational amplifier is a dummy ground point, that is, u1=0. The input terminal of the ion collecting electrode is connected to the inverting input terminal u1 of the inverting amplifier. According to the principle of dummy ground, the potential of the ion collecting electrode is 0, thereby ensuring the collection of ions.

The operation of the detection device for an ion count in tumor-related molecules comprises steps:

1) vacuumizing: during which, the first solenoid valve is turned on, and the ionization chamber is vacuumized by the vacuum generator until the degree of vacuum inside the ionization chamber reaches a set standard;

2) starting pre-heating of the filament to generate an electron source: during which, the ionization high voltage is turned on, and the filament is connected to a negative pole of a high-voltage electric field so that the filament (hot cathode), after being powered on and heated, emits electrons to the ionization chamber to form a stream of electrons;

3) accelerating the electrons: during which, a positive voltage is applied onto the high-voltage accelerating electrode, the positive voltage, serving as an accelerating electrode high voltage, draws and accelerates the electrodes emitted by the filament, and the accelerated electrons are repelled by the ion collecting electrode after passing through the high-voltage accelerating electrode of a net structure since a voltage at the ion collecting electrode is negative with respect to the high-voltage accelerating electrode, and then return to the high-voltage accelerating electrode in an accelerated speed;

4) ionizing the air: during which, the probability of collision of the electrons with air molecules is increased in the return motion of the electrons so that more air molecules are ionized to become positive ions and secondary electrons, and the electronic interaction between the high-speed electrons and the tumor-related molecules in atomic orbits is realized by regulating the high-voltage electric field since the orbital electrons (for example, K, L and M orbits) outside the nucleus have their own characteristic energy levels; and the electrons are forced out of the orbits to obtain ions having an energy spectrum representative of characteristics of the orbits; and 5) ion counting: during which, the positive ions are drawn by the ion collecting electrode with a lowest potential; an induced voltage is formed on the ion collecting electrode of a graphene structure, and the induced voltage is related to corresponding ions; and the induced voltage is passed to the ion counter which makes a corresponding determination, so far one measurement is completed.

In the step 4), when an air sample to be tested is found in the air sample chamber, the CPU controls to turn on the first solenoid valve (this duration is very short, in milliseconds), and turn off the first solenoid valve when the air is fed to the ionization chamber; and in the step 5), when the ionization high voltage is turned on, the ion counter starts counting, and at the end of counting, an ion count curve corresponding to related molecules is shown in a display; and the vacuum generator is configured to maintain the measurement condition in the ionization chamber. If the exhaled air contains certain tumor-related molecules, the content of the tumor-related molecules is shown in the ion count chart. The ionization high voltage can be regulated arbitrarily. The filament current is regulated correspondingly, when the ionization high voltage is regulated. For example, the ionization high voltage can be linearly increased from 100V to 100 KV. Different related molecules may have count peaks in different high voltage ranges. Since different ionization high voltages correspond to different tumor molecules, the type of tumor molecules can be determined according to the value of the applied ionization high voltage. The concentration of tumor molecules can be determined according to the peak of the ion counter. Thus, the type and development of tumors can be determined.

The present invention has the following beneficial effects. The present invention provides a detection device for an ion count in tumor-related molecules and a usage method thereof, by which the type and development of tumors can be quickly detected simply by detecting the air exhaled by a subject. Compared with other detection methods, it is low in cost and fast, free of any injury to the subject. Furthermore, by the detection device, early-stage cancers can be detected. This is a tremendous contribution to the health of the human beings and also to the development of cancer treatment means.

DETAILED DESCRIPTION OF THE PRESENT INVENTION

The present invention will be further described below in detail with reference to the accompanying drawings.

Figure 1:
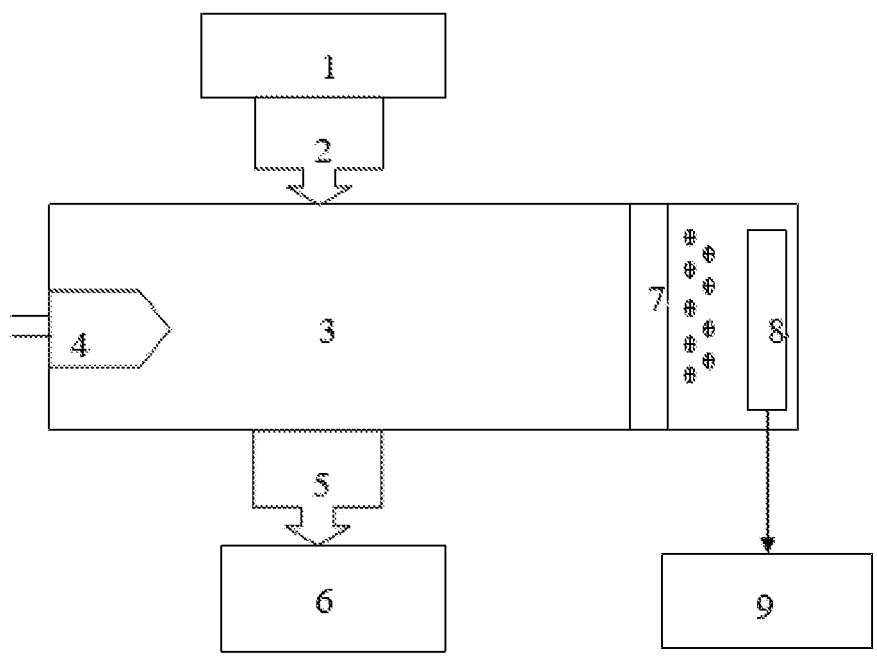
FIG. 1 is a structural diagram of a detection device for an ion count in tumor-related molecules.

FIG. 1 is a structural diagram of a detection device for an ion count in tumor-related molecules, according to the present invention. The detection device comprises an air sample chamber 1, a first solenoid valve 2, an ionization chamber 3, a filament 4, a second solenoid valve 5, a vacuum generator 6, a high-voltage accelerating electrode 7, an ion collecting electrode 8 and an ion counter 9. The air sample chamber 1 is connected to the ionization chamber 3 through the first solenoid valve 2. The filament 4 is arranged at a left end of the ionization chamber 3. A lower end of the ionization chamber 3 is connected to the vacuum generator 6 through the second solenoid valve 5. The high-voltage accelerating electrode 7 and the ion collecting electrode 8 are successively arranged at a right end of the ionization chamber 3. The ion collecting electrode 8 is connected to the ion counter 9.

Figure 2:
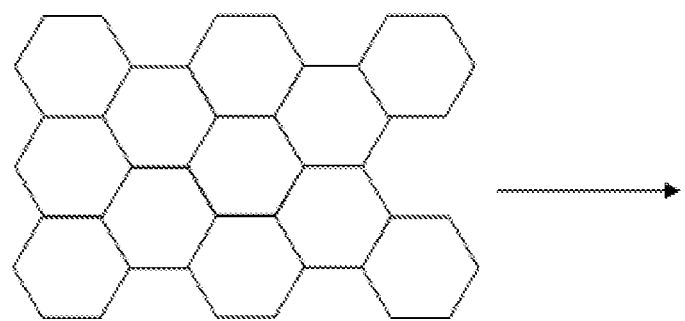
FIG. 2 is a schematic view of a hexagonal lattice of carbon atoms in graphene.

The air sample chamber 1 is configured to collect the air exhaled by a subject. The first solenoid valve 2 is communicated with the air sample chamber 1 and the ionization chamber 3, and configured to control the flow of the air from the air sample chamber 1 to the ionization chamber 3 The filament 4 is connected to a negative pole of a high-voltage electric field, to serve as a cathode. The high-voltage accelerating electrode 7 is of a net structure. This is advantageous for the passing of electrons. The ion collecting electrode 8 is a graphene electrode, the specific structure of which is shown in FIG. 2. Graphene is quite stable in structure, since it is an elemental carbon formed by the neat arrangement of carbon atoms in a hexagonal lattice. Graphene has only one layer of atoms. The motion of electrons is limited in one plane. It is quite suitable to be used as an ion collecting electrode.

Figure 3:
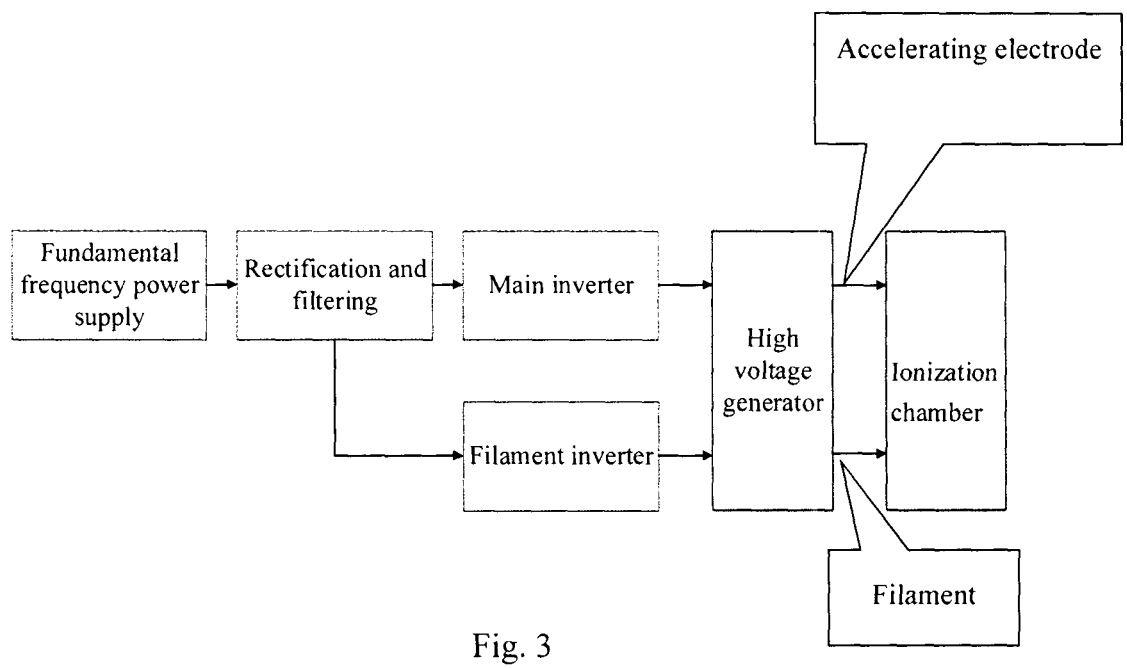
FIG. 3 is a circuit diagram of a detection device for an ion count, using a fundamental frequency power supply.

FIG. 3 is a circuit diagram of a detection device for an ion count, using a fundamental frequency power supply. A fundamental frequency power supply is rectified and filtered to obtain a DC voltage; the DC voltage is converted into a high-frequency voltage by a main inverter circuit; the high-frequency voltage is passed to a primary side of a high-voltage transformer in a high-voltage generator and boosted by the high-voltage transformer; and the AC high-frequency voltage obtained at the primary side is converted into a constant DC high-voltage by voltage-doubling rectification. The constant DC high-voltage is the accelerating electrode high voltage. A high-voltage accelerating electrode sampling signal is compared with a set value in real time. An error signal controls, after pulse width modulation, the ON time of an inverter bridge, in order to ensure the actual value of the accelerating electrode is equal to the set value. A fundamental frequency power supply is rectified and filtered to obtain a DC voltage, the DC voltage is passed to a filament inverter circuit and then to the primary side of a filament transformer, and the output from the primary side is used as the filament heating voltage. The filament heating current is regulated by PWM. During the measurement, the current sampling signal of the filament is compared with a set value in real time. An error signal controls, after pulse width modulation, the width of the inversion trigger pulse of the filament, in order to ensure the actual value is equal to the set value. The voltage value of the accelerating electrode high voltage is regulated, tumor molecules are ionized by different voltages, and the result of ionization is analyzed by the ion counter. In this way, the sorted detection of tumor-related molecules is completed.

The filament heating circuit functions to emit electrons. The measurement current for the ionization chamber is related to two factors: the filament current and the accelerating electrode voltage. When the accelerating electrode voltage changes, the strength of the in-line accelerated electric field changes, the capability of the accelerating electrode in collecting electrons changes correspondingly, so that the accelerating electrode current changes. The change in the voltage of the filament causes the change in the current of the filament, directly influencing the efficiency of emitting electrons by the filament. The degree of vacuum inside the ionization chamber is maintained above 10-6 mmHg, in order to ensure the normal heating of the filament and the speed of the electrons flying to the anode.

The measurement current in the ionization chamber is determined by the current of the high-voltage accelerating electrode. The current of the high-voltage accelerating electrode depends upon the number of electrons emitted by the filament in a unit time. The number of electrons emitted by the filament is determined by the temperature of the filament. At a higher temperature of the filament, more electrons will be emitted by the filament. The temperature of the filament is determined by the filament heating voltage in the ionization chamber. Under a higher filament heating voltage, the temperature of the filament will be higher. In order to ensure the precision of ion counting, the current for the filament and the high-voltage accelerating electrode in the ionization chamber is always maintained unchanged.

Figure 4:
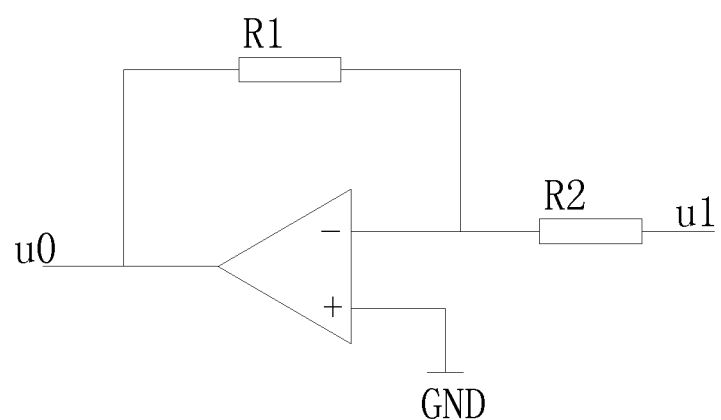
FIG. 4 is a schematic view of an inverting amplifier.

The measurement circuit is an inverting amplifier consisting of operational amplifiers, as shown in FIG. 4. Its in-phase input terminal is grounded. According to the principle of dummy ground, the potential of its inverting input terminal is also 0, thereby ensuring that the potential of the ion collecting electrode is 0. As an important characteristic of a deep parallel voltage negative feedback amplifier, "dummy ground" means that the input terminal of an integrated operational amplifier is a dummy ground point, that is, u1=0. The input terminal of the ion collecting electrode is connected to the inverting input terminal u1 of the inverting amplifier. According to the principle of dummy ground, the potential of the ion collecting electrode is 0, thereby ensuring the collection of ions.

The operation of the detection device for an ion count in tumor-related molecules comprises steps:

1) vacuumizing: during which, the first solenoid valve 2 is turned on, and the ionization chamber is vacuumized by the vacuum generator until the degree of vacuum inside the ionization chamber reaches a set standard;

2) starting pre-heating of the filament to generate an electron source: during which, the ionization high voltage is turned on, and the filament is connected to a negative pole of a high-voltage electric field so that the filament 4 (hot cathode), after being powered on and heated, emits electrons to the ionization chamber 3 to form a stream of electrons;

3) accelerating the electrons: during which, a positive voltage is applied onto the high-voltage accelerating electrode 7, the positive voltage, serving as an accelerating electrode high voltage, draws and accelerates the electrodes emitted by the filament 4, and the accelerated electrons are repelled by the ion collecting electrode 8 after passing through the high-voltage accelerating electrode (7) of a net structure since a voltage at the ion collecting electrode 8 is negative with respect to the high-voltage accelerating electrode 7, and then return to the high-voltage accelerating electrode 7 in an accelerated speed;

4) ionizing the air: during which, the probability of collision of the electrons with air molecules is increased in the return motion of the electrons so that more air molecules are ionized to become positive ions and secondary electrons, and the electronic interaction between the high-speed electrons and the tumor-related molecules in atomic orbits is realized by regulating the high-voltage electric field since the orbital electrons (for example, K, L and M orbits) outside the nucleus have their own characteristic energy levels; and the electrons are forced out of the orbits to obtain ions having an energy spectrum representative of characteristics of the orbits; and 5) ion counting: during which, the positive ions are drawn by the ion collecting electrode with a lowest potential; an induced voltage is formed on the ion collecting electrode of a graphene structure, and the induced voltage is related to corresponding ions; and the induced voltage is passed to the ion counter which makes a corresponding determination, so far one measurement is completed.

Figure 5:
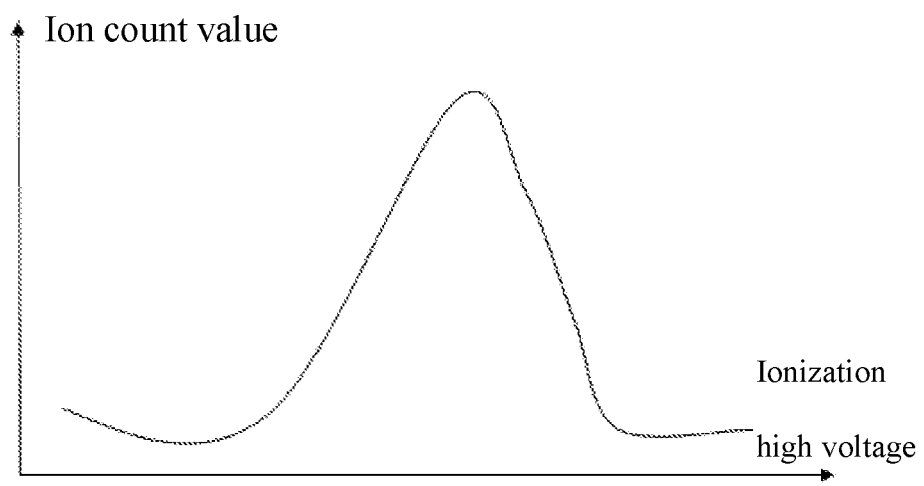
FIG. 5 is an ion count chart of tumor-related molecules, in which:
1: gas sample chamber;
2: first solenoid valve;
3: an ionization chamber;
4: filament;
5: a second solenoid valve;
6: vacuum generator;
7: high-pressure accelerating electrode;
8: ion collecting electrode; and
9: ion counter.

In the step 4), when an air sample to be tested is found in the air sample chamber, the CPU controls to turn on the first solenoid valve 2 (this duration is very short, in milliseconds), and turn off the first solenoid valve 2 when the air is fed to the ionization chamber; and in the step 5), when the ionization high voltage is turned on, the ion counter starts counting, and at the end of counting, an ion count curve corresponding to related molecules is shown in a display; and the vacuum generator is configured to maintain the measurement condition in the ionization chamber. FIG. 5 is an ion count chart of tumor-related molecules. It can be found from FIG. 5 that, if the exhaled air contains certain tumor-related molecules, the content of the tumor-related molecules is shown in the ion count chart. The ionization high voltage can be regulated arbitrarily. The filament current is regulated correspondingly, when the ionization high voltage is regulated. In this embodiment, the ionization high voltage is linearly increased from 100V to 100 KV. Different related molecules may have count peaks in different high voltage ranges. Since different ionization high voltages correspond to different tumor molecules, the type of tumor molecules can be determined according to the value of the applied ionization high voltage. The concentration of tumor molecules can be determined according to the peak of the ion counter. Thus, the type and development of tumors can be determined.

The foregoing descriptions are merely some implementations of the present invention. It should be noted that, to a person of ordinary skill in the art, various improvements and modifications may be made without departing from the creative concept of the present invention, and these improvements and modifications shall be deemed as falling into the protection scope of the present invention.

What is claimed is:

1. A detection device for an ion count in tumor-related molecules, comprising an air sample chamber (1), a first solenoid valve (2), an ionization chamber (3), a filament (4), a second solenoid valve (5), a vacuum generator (6), a high-voltage accelerating electrode (7), an ion collecting electrode (8) and an ion counter (9), wherein the air sample chamber (1) is connected to the ionization chamber (3) through the first solenoid valve (2); the filament (4) is arranged at a left end of the ionization chamber; a lower end of the ionization chamber (3) is connected to the vacuum generator (6) through the second solenoid valve (5); the high-voltage accelerating electrode (7) and the ion collecting electrode (8) are successively arranged at a right end of the ionization chamber (3); the ion collecting electrode (8) is connected to the ion counter (9); the air sample chamber (1) is configured to collect the air exhaled by a subject; the first solenoid valve (2) is communicated with the air sample chamber (1) and the ionization chamber (3), and configured to control the flow of the air from the air sample chamber (1) to the ionization chamber (3); and the filament (4) is connected to a negative pole of a high-voltage electric field, to serve as a cathode.

2. The detection device for an ion count in tumor-related molecules according to claim 1, wherein the high-voltage accelerating electrode (7) is of a net structure.

3. The detection device for an ion count in tumor-related molecules according to claim 1, wherein the ion collecting electrode (8) is a graphene electrode.

4. A method for using the detection device for an ion count in tumor-related molecules according claim 1, comprising steps:
   1) vacuumizing: during which, the second solenoid valve (5) is turned on, and the ionization chamber (3) is vacuumized by the vacuum generator (6) until the degree of vacuum inside the ionization chamber (3) reaches a set standard;
   2) starting pre-heating of the filament (4) to generate an electron source: during which, the ionization high voltage is turned on, and the filament (4) is connected to a negative pole of a high-voltage electric field so that the filament (4), after being powered on and heated, emits electrons to the ionization chamber (3) to form a stream of electrons;
   3) accelerating the electrons: during which, a positive voltage is applied onto the high-voltage accelerating electrode (7), the positive voltage, serving as an accelerating electrode high voltage, draws and accelerates the electrodes emitted by the filament (4), and the accelerated electrons are repelled by the ion collecting electrode (8) after passing through the high-voltage accelerating electrode (7) since a voltage at the ion collecting electrode (8) is negative with respect to the high-voltage accelerating electrode (7), and then return to the high-voltage accelerating electrode (7) in an accelerated speed;
   4) ionizing the air: during which, the probability of collision of the electrons with air molecules is increased in the return motion of the electrons so that more air molecules are ionized to become positive ions and secondary electrons, and the electronic interaction between the high-speed electrons and the tumor-related molecules in atomic orbits is realized by regulating the high-voltage electric field since the orbital electrons outside the nucleus have their own characteristic enemy levels; and the electrons are forced out of the orbits to obtain ions having an energy spectrum representative of characteristics of the orbits; and 5) ion counting: during which, the positive ions are drawn by the ion collecting electrode (8) with a lowest potential; an induced voltage is formed on the ion collecting electrode (8), and the induced voltage is related to corresponding ions; and the induced voltage is passed to the ion counter (9) which makes a corresponding determination, so far one measurement is completed.

5. The method for using the detection device for an ion count in tumor-related molecules according to claim 4, wherein, in the step 4), when an air sample to be tested is found in the air sample chamber (1), the CPU controls to turn on the first solenoid valve (2), and turn off the first solenoid valve (2) when the air is fed to the ionization chamber (3); and in the step 5), when the ionization high voltage is turned on, the ion counter (9) starts counting, and at the end of counting, an ion count curve corresponding to related molecules is shown in a display; and the vacuum generator (6) is configured to maintain the measurement condition in the ionization chamber.

6. The method for using the detection device for an ion count in tumor-related molecules according to claim 5, further comprising sorted detection of tumor-related molecules, comprising: regulating a voltage value of the accelerating electrode high voltage, ionizing tumor molecules by different voltages, and analyzing the result of ionization by the ion counter (9).

* * * * *